(12) United States Patent
Jansen et al.

(10) Patent No.: US 6,673,949 B2
(45) Date of Patent: Jan. 6, 2004

(54) PROCESS FOR THE EPOXIDATION OF HYDROCARBONS

(75) Inventors: Ursula Jansen, Neuss (DE); Andreas Wegner, Müheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 12 days.

(21) Appl. No.: 10/214,073

(22) Filed: Aug. 7, 2002

(65) Prior Publication Data

US 2003/0040635 A1 Feb. 27, 2003

(30) Foreign Application Priority Data

Aug. 10, 2001 (DE) .......................................... 101 39 531

(51) Int. Cl.⁷ ............................................ C07D 301/08
(52) U.S. Cl. ....................................................... 549/523
(58) Field of Search ......................................... 549/523

(56) References Cited

U.S. PATENT DOCUMENTS

| | | | |
|---|---|---|---|
| 5,547,905 A | 8/1996 | Kulsrestha et al. | 502/66 |
| 5,623,090 A | 4/1997 | Haruta et al. | 568/360 |
| 6,087,299 A | 7/2000 | Grub et al. | 933/347 |
| 6,103,915 A | 8/2000 | Arca et al. | 830/531 |

OTHER PUBLICATIONS

Indian Chem. Eng. (month unavailable) 1987, Max Appl, pp. 7–29, "Ammonia Synthesis and the Development of Catalytic and High–pressure Processes in the Chemical Industry".

*Primary Examiner*—Taofiz A Solola
(74) *Attorney, Agent, or Firm*—Joseph C. Gil; N. Denise Brown; John E. Mrozinski, Jr.

(57) ABSTRACT

The present invention relates to a process for the epoxidation of hydrocarbons. This process comprises reacting at least one hydrocarbon with oxygen or air or nitrous oxide or other gaseous oxidants, in the presence of a mixture comprising at least two elements selected from the group consisting of Sc, Y, Ti, Zr, Hf, V, Nb, Ta, Cr, Mo, W, Re, Fe, Co, Ni, Sn, Pb, Sb, Bi and Se, on a support with a BET surface area of less than 200 $m^2/g$. The present invention also relates to catalysts suitable for the epoxidation of hydrocarbons, wherein the catalyst comprises a mixture comprising at least two metals selected from the group consisting of Sc, Y, Ti, Zr, Hf, V, Nb, Ta, Cr, Mo, W, Re, Fe, Co, Ni, Sn, Pb, Sb, Bi and Se, on a support with a BET surface area of less than 200 $m^2/g$.

7 Claims, No Drawings

PROCESS FOR THE EPOXIDATION OF HYDROCARBONS

BACKGROUND OF THE INVENTION

The present invention relates to a process for the epoxidation of hydrocarbons. This process comprises reacting at least one hydrocarbon with oxygen, in the presence of a mixture comprising at least two elements selected from the group consisting of Sc, Y, Ti, Zr, Hf, V, Nb, Ta, Cr, Mo, W, Re, Fe, Co, Ni, Sn, Pb, Sb, Bi and Se, on a support with a BET surface area of less than 200 $m^2/g$. The present invention also relates to catalysts suitable for the epoxidation of hydrocarbons. These catalysts comprise a mixture comprising at least two elements from the group consisting of Sc, Y, Ti, Zr, Hf, V, Nb, Ta, Cr, Mo, W, Re, Fe, Co, Ni, Sn, Pb, Sb, Bi and Se, on a support with a BET surface area of less than 200 $m^2/g$.

Epoxides are an important starting material in the polyurethane industry. There are a number of processes given for preparing these, some of which have also been converted to the industrial scale. Currently, the direct oxidation of ethylene with air or with gases which contain molecular oxygen in the presence of a silver-containing catalyst, as described in EP-A2-933 130, is used for the industrial preparation of ethylene oxide. In order to prepare longer-chain epoxides on an industrial scale, hydrogen peroxide or hypochlorite in the liquid phase are generally used as oxidizing agents. EP-A1-0 930 308 describes, for example, the use of ion exchanged titanium silicalites as a catalyst with these two oxidizing agents.

Another class of oxidation catalysts, which enables propylene to be oxidized to the corresponding epoxide in the gas phase, was disclosed recently in, for example, U.S. Pat. No. 5,623,090. Here, gold on anatase is disclosed as a catalyst, oxygen serves as the oxidizing agent and this is used in the presence of hydrogen. The system is characterized by extraordinarily high selectivity (i.e. S>95%) with respect to propylene oxidation. The low conversion and deactivation of the catalyst are, Very little information is disclosed in the literature about other active components, apart from gold and silver, for the selective direct oxidation of propylene and higher alkenes in the gas phase.

Since none of the published catalysts has previously exhibited satisfactory results with regard to activity and selectivity for the direct oxidation of propylene to propylene oxide, other active components are being sought as alternatives to the known silver and gold-containing catalysts. An important prerequisite is that the oxidation process does not go to completion, and form the corresponding acid or the aldehyde or ketone. Rather, any suitable the oxidation process must terminate at the epoxide stage.

A few mixtures of elements from groups 3–10 or 14–16 in the Periodic System of Elements according to IUPAC 1986 have already been disclosed in the literature.

For example, mixtures of iron, cobalt and nickel on a variety of supports are used to prepare ammonia. To provide an example of the very extensive literature, reference is made here only to the review by M. Appl [Indian Chem. Eng., 1987, 7–29]. Furthermore, mixtures of iron and cobalt are also known and described as being suitable for the oxidation of cyclohexane to adipic acid. See, for example, U.S. Pat. No. 5,547,905. The formation of epoxides is not disclosed by this reference, however.

It has now surprisingly been shown that propylene oxide can be prepared by the direct oxidation of propylene with oxygen or air, using mixtures of different elements. This is all the more unusual because the oxidation remains at the epoxide stage, and does not produce the corresponding acids, ketones or aldehydes.

SUMMARY OF THE INVENTION

The invention provides a process for the epoxidation of hydrocarbons. This process comprises (1) reacting
   (a) at least one hydrocarbon,
with
   (b) oxygen, or air or nitrous oxide or other gaseous oxidents (preferably oxygen)
in the presence of
   (c) a mixture comprising at least two elements selected from the group consisting of Sc, Y, Ti, Zr, Hf, V, Nb, Ta, Cr, Mo, W, Re, Fe, Co, Ni, Sn, Pb, Sb, Bi and Se, on an inert support with a BET surface area of less than 200 $m^2/g$.

Said elements may be present as such or in the form of chemical compounds. The present invention also relates to suitable epoxidation catalysts for hydrocarbons. These epoxidation catalysts comprise:

(i) a mixture comprising at least two elements selected from the group consisting of Sc, Y, Ti, Zr, Hf, V, Nb, Ta, Cr, Mo, W, Re, Fe, Co, Ni, Sn, Pb, Sb, Bi and Se, (ii) on an inert support with a BET surface area of less than 200 $m^2/g$. Said elements may be present as such or in the form of chemical compounds.

DETAILED DESCRIPTION OF THE INVENTION

As used herein, the expression hydrocarbon is understood to cover unsaturated or saturated hydrocarbons, such as, for example, olefins or alkanes which may also contain heteroatoms such as N, O, P, S or halogen atoms. These organic hydrocarbon components which are to be oxidized in accordance with the present invention may be acyclic, monocyclic, bicyclic or polycyclic, and may be monoolefinic, diolefinic or polyolefinic. In the case of organic hydrocarbon components with two or more double bonds, the double bonds may be conjugated or non-conjugated. It is preferred that the hydrocarbons which are oxidized in accordance with the present invention, form oxidation products with partial pressures which are low enough, at the reaction temperature, to enable constant removal of the product from the catalyst.

Unsaturated and saturated hydrocarbons with 2 to 20, preferably 3 to 10 carbon atoms, are preferred for the present invention. In particular, hydrocarbons such as, for example, propylene, propane, isobutane, isobutylene, 1-butene, 2-butene, cis-2-butene, trans-2-butene, 1,3-butadiene, pentene, pentane, 1-hexene, hexane, hexadiene, cyclohexene, benzene, are preferred.

The oxygen used in the present invention may be in a very wide variety of forms. Suitable forms of oxygen include those such as, for example, molecular oxygen, air and nitrogen oxide. Molecular oxygen is preferred.

Suitable mixtures of at least two elements for the epoxidation catalysts of the present invention include preferably binary mixtures of the metals selected from the group consisting of Sc, Y, Ti, Zr, Hf, V, Nb, Ta, Cr, Mo, W, Re, Fe, Co, Ni, Sn, Pb, Sb, Bi and Se.

It may be advantageous to add conventional promoters or moderators to the element mixture, such as alkaline earth and/or alkali metal ions such as, for example, the hydroxides, carbonates, nitrates, chlorides of one or more alkaline earth and/or alkali metals and/or silver. These are described in EP-A1-0 933 130 on page 4, lines 39 et. seq., which is believed to correspond to U.S. Pat. No. 6,087,299, the disclosure of which is herein incorporated by reference.

The different elements and promoters in the mixtures can be in the range from 0 to 100% by weight of the total weight of the active ingredients, preferably from 0.01 to 99.99%, even more preferably in the range from 0.1 to 99.9% with the sum of all elements in the mixture totalling 100% by weight. The preferred range for the promoters is from 0.001 to 35% by weight of the total weight of the active ingredients. Preferred mixtures of elements to be used in the present invention include mixtures comprising: CoFe, CoRe, CoCo, CoNi, NiCr, Co—Fe, Co—Re, Co—Cr, Co—Ni, Ni—Cr, Sb—Fe, Co—Fe—Ag, Co—Pb—Ag, Ni—Pb—Ag, Ni—Co—Ag, Co—Fe—Sr—Ag, Co—Pb—Sr—Ag, Co—Pb—Fe—Ag, Co—Cs—Fe—Ag, Co—Cs—Pb—Ag, Co—Ba—Bi—Ag, Ni—Pb—Fe—Ag, Ni—Cs—Fe—Ag, Ni—Cs—Pb—Ag, Ni—Ba-Fe—Ag, Ni—Ba—Pb—Ag, Ni—Co—Sr—Ag, Ni—Co—Fe—Ag, Eu—Er—Pb—W, Mo—Pb—Sr—Ag, Fe—Pb—Sr—Ag, Fe—Pb—Sr—Re, Fe—Mo—Sr—Ag, Cr—Sr—Re—Ag, Cr—Fe—Re—Ag, Cr—Fe—Sr—Ag, Cr—Fe—Pb—Ag, Cr—Fe—Mo—Pb, Co—Fe—Sr—Ag, Co—Cr—Re—Ag, Co—Cr—Pb—Re, Co—Cr—Pb—Sr, Co—Cr—Mo—Ag, Co—Cr—Fe—Sr, Co—Cr—Fe—Pb, Co—Cr—Fe—Mo, Co—K—Pb—Ag, Co—Nd—Pb—Ag, Co—Fe—Pb—Ag, Co—Fe—K—Ag, Co—Cs—Pb—Ag, Co—Cs—Fe—Ag and SbFe.

Suitable supports for the element mixtures which are used to form the epoxidation catalysts for the present invention are compounds with BET surface areas of from <200 $m^2/g$, preferably <100 $m^2/g$, more preferably <10 $m^2/g$ and most preferably <1 $m^2/g$. It is preferred that the supports comprise compounds selected from the group consisting of $Al_2O_3$, $SiO_2$, $CeO_2$ and $TiO_2$. Of course, these compounds must satisfy the above stated requirements for BET surface areas to be suitable supports for the present invention.

It is preferred that the porosity of the supports is from 20 to 60% (by volume of the support), most preferably from 30 to 50%.

The particle size of the support is governed by the process conditions for gas phase oxidation. Generally, suitable particle sizes are in the range $\frac{1}{10}$ to $\frac{1}{20}$ of the reactor diameter.

The specific surface area of the support is determined in the usual way using Brunauer, Emmet and Teller's method as described in J. Am. Chem. Soc. 1938, 60, 309 (DIN 66 131). The porosity of the support is determined by mercury porosimetry, and the particle sizes of the element particles on the support surface are assessed by means of electron microscopy and X-ray diffractometry.

The element concentration on the support should generally be in the range of 0.001 to 50% by weight (based on the total weight of the combined elements and the support), preferably of 0.001 to 20% by weight, and most preferably of 0.01 to 10% by weight.

Production of the element particles on the support is not restricted to one method. A few examples of suitable processes for generating metal particles which may be mentioned here include those methods such as, for example, deposition-precipitation, as described in EP-B-0 709 360 on p. 3, lines 38 et seq., believed to correspond to U.S. Pat. No. 5,623,090, the disclosure of which is herein incorporated by reference, impregnation in solution, incipient wetness, colloid processes, sputtering chemical vapour deposition (CVD) and physical vapour deposition (PVD).

Incipient wetness is understood to be the addition of a solution containing soluble element compounds to the support material, wherein the volume of the solution on the support is less than or equal to the pore volume of the support. Thus, the support remains dry on a macroscopic scale. Any solvent in which the element precursor is soluble may be used as a solvent for incipient wetness, Suitable solvents include compounds such as, for example, water, alcohols, (crown) ethers, esters, ketones, halogenated hydrocarbons, etc.

The support is preferably soaked with a solution containing the element ions and then dried and reduced. Furthermore, the solution may also contain components known to a person skilled in the art which can increase the solubility of the element salt(s) in the solvent and which alter the redox potential(s) of the element(s) and/or the pH. Ammonia, amines, diamines, hydroxyamines and acids such as HCl, $HNO_3$, $H_2SO_4$, $H_3PO_4$, may be mentioned in particular.

1. Soaking may take place by incipient wetness, but it is not restricted to this method. The incipient wetness process can include the following steps:
   single coating with one element and/or multiple coating with another element,
   single coating with some of the elements or with all the elements in one step,
   multiple coating with several elements in one or more steps in sequence,
   multiple coating with several elements alternately in one or more steps.

2. Drying the support with active components obtained after step 1 at a temperature of about 40 to about 200° C., at atmospheric pressure or also reduced pressure. At atmospheric pressure, the process may be performed under an atmosphere of air or also under an inert gas atmosphere (e.g. Ar, $N_2$, He et al.). The drying time is in the range of from 2 to 24 h, preferably of from 4 to 8 h.

3. Calcining the catalyst precursors obtained after step 2 under an inert gas atmosphere, and subsequently/ exclusively under a gas atmosphere which contains oxygen. The concentration of oxygen in the gas stream is advantageously in the range 0 to 21 vol. % (based on the total volume of the gas stream), preferably 5 to 15 vol. %.

The temperature for calcination is adapted to the element mixture, and is therefore generally in the range 400 to 600° C., preferably 450 to 550° C., and particularly preferably 500° C.

4. Reducing the catalyst precursors obtained after step 2 and/or 3 at elevated temperature under a nitrogen atmosphere which contains hydrogen. The concentration of hydrogen may be between 0 and 100 vol. %, but is preferably 0 to 25 vol. % (based on the total volume of the gas stream), and more preferably 5 vol. %. The reducing temperatures are adapted to the particular element mixture and are between 100 and 600° C.

Conventionally, the epoxidation process is performed, preferably in the gas phase, under the following conditions:

The molar amounts of the hydrocarbon used, with respect to the total number of moles of hydrocarbon, oxygen and optionally diluent gas, and the relative molar ratios of the components may be varied over a wide range. These molar amounts and ratios are generally governed by the explosion limit of the hydrocarbon/oxygen mixture. The process is generally performed either above or below the explosion limit.

An excess of hydrocarbon, with respect to the oxygen used (on a molar basis), is preferably used. The hydrocarbon concentration in the oxygen is typically either $\leq 2$ mol. %, or $\geq 78$ mol. % (based on the total mols in the gas stream). Hydrocarbon concentrations in the range of 0.5 to 2 mol. % when working below the lower explosion limit are preferably chosen, and concentrations in the range of 78 to 99 mol. % when working above the upper explosion limit are preferably chosen. The ranges of 1 to 2 mol. %, and of 78 to 90 mol. %, respectively, are particularly preferred.

The molar proportion of oxygen, with respect to the total number of moles of hydrocarbon, oxygen and diluent gas, may be varied over a wide range. Oxygen is preferably used in a molar deficiency with respect to the hydrocarbon. Oxygen is preferably used within the range of 1 to 21 mol. % (based on the total mols in the gas stream), and most preferably of 5 to 21 mol. %.

In addition to the hydrocarbon and oxygen, a diluent gas such as, for example, nitrogen, helium, argon, methane, carbon dioxide, carbon monoxide or another similar gas which behaves in a largely inert manner, may also be used. Mixtures of the inert components described above may also be used. The addition of an inert component is beneficial for the transport of the heat which is evolved during this exothermic oxidation reaction, and for safety purposes. When a diluent gas is present, it is also possible to use compositions for the reactant gas mixtures within the range of the explosion limits of the undiluted mixtures of hydrocarbon and oxygen.

The contact time for hydrocarbon and catalyst is generally in the range of 5 to 60 seconds.

In general, the process is performed at temperatures in the range of 120 to 300° C., preferably of 180 to 250° C.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

2.468 g of cobalt nitrate were dissolved in 3 ml of water. This solution was added to about 10 g of $Al_2O_3$, and was allowed to be absorbed by the $Al_2O_3$. The solid obtained in this way was dried for 4 h at 100° C. in a vacuum drying cabinet under a vacuum of about 15 mm Hg.

Then 0.042 g of rhenic acid were dissolved in 4.5 ml of water. This solution was allowed to be fully absorbed by the previously prepared solid and dried overnight at about 15 mm Hg and 100° C. in a vacuum drying cabinet.

Finally, the precursor prepared in this way was reduced for 12 h at 500° C. using 10 vol. % $H_2$ in $N_2$ flowing at 60 l/h.

After reduction, 10 g of the catalyst obtained in this way was tested in a continuously operated fixed bed reactor with a residence time of about 20 sec., under a reactant gas composition of 79 vol. % propylene and 21 vol. % oxygen. At an internal temperature of 230° C., PO concentrations of about 60 ppm were determined in the exit gas stream.

Example 2

2.468 g of cobalt nitrate were dissolved in 3 ml of water, and this solution was allowed to be absorbed by about 10 g of $Al_2O_3$. The solid obtained in this way was dried for 4 h at 100° C. in a vacuum drying cabinet under a vacuum of about 15 mm Hg.

Then 0.202 g of chromium nitrate were dissolved in 4.5 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 215° C., PO concentrations of about 90 ppm were determined in the exit gas stream.

Example 3

1.298 g of cobalt nitrate were dissolved in 4 ml of water, and this solution was allowed to be absorbed by about 10 g of $Al_2O_3$. The solid obtained in this way was dried for 4 h at 100° C. in a vacuum drying cabinet under a vacuum of about 15 mm Hg.

Then, 2.02 g of chromium nitrate were dissolved in 4 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 220° C., PO concentrations of about 40 ppm are determined in the exit gas stream.

Example 4

1.303 g of nickel nitrate were dissolved in 4 ml of water, and this solution was allowed to be absorbed by about 10 g of $Al_2O_3$. The solid obtained in this way was dried for 4 h at 100° C. in a vacuum drying cabinet under a vacuum of about 15 mm Hg.

Then, 1.299 g of cobalt nitrate were dissolved in 4.5 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 225° C., PO concentrations of about 40 ppm were determined in the exit gas stream.

Example 5

0.13 g of nickel nitrate were dissolved in 4.5 ml of water, and this solution was allowed to be absorbed by 10 g of $Al_2O_3$. The solid obtained in this way was dried for 4 h at 100° C. in a vacuum drying cabinet under a vacuum of about 15 mm Hg.

Then, 2.468 g of cobalt nitrate were dissolved in 4 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 225° C., PO concentrations of about 35 ppm were determined in the exit gas stream.

Example 6

2.475 g of nickel nitrate were dissolved in 3.0 ml of water and this solution was allowed to be absorbed by 10 g of $Al_2O_3$. The solid obtained in this way was dried for 4 h at 100° C. in a vacuum drying cabinet under a vacuum of about 15 mm Hg.

Then, 0.202 g of chromium nitrate were dissolved in 4.5 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 200° C., PO concentrations of about 310 ppm were determined in the exit gas stream.

Example 7

2.468 g of cobalt nitrate were dissolved in 3 ml of water, and this solution was allowed to be absorbed by 10 g of $Al_2O_3$. The solid obtained in this way was dried for 4 h at 100° C. in a vacuum drying cabinet under a vacuum of about 15 mm Hg.

Then, 0.19 g of iron nitrate were dissolved in 4.5 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 225° C., PO concentrations of about 45 ppm were determined in the exit gas stream

Example 8

0.129 g of cobalt nitrate were dissolved in 4.5 ml of water, and this solution was allowed to be absorbed by 10 g of $Al_2O_3$. The solid obtained in this way was dried for 4 h at 100° C. in a vacuum drying cabinet under a vacuum of about 15 mm Hg.

Then, 2.475 g of nickel nitrate were dissolved in 3 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 215° C., PO concentrations of about 15 ppm were determined in the exit gas stream

Example 9

0.646 g of antimony chloride were dissolved in 4.5 ml of ethanol, and this solution was allowed to be absorbed by 10 g of $Al_2O_3$. The solid obtained in this way was dried for 4 h at 100° C. in a vacuum drying cabinet under a vacuum of about 15 mm Hg.

Then, 1.9 g of iron nitrate were dissolved in 3.5 ml of water. This solution was allowed to be fully absorbed by the previously prepared solid, and dried overnight at about 15 mm Hg and 100° C. in a vacuum drying cabinet.

Finally, the solid was reduced for about 8 h at 500° C. using 10 vol. % $H_2$ in $N_2$ flowing at 60 l/h.

After reduction, about 10 g of the catalyst obtained in this way were tested in a continuously operated fixed bed reactor with a residence time of about 20 sec., under a reactant gas composition of 79 vol. % propylene and 21 vol. % oxygen. At an internal temperature of 225° C., PO concentrations of about 30 ppm were determined in the exit gas stream.

Examples 10 to 50

Preparation of Examples 10–50

The catalysts used in examples 10–50 were prepared using the incipient wetness method. Aqueous solutions of the elements were prepared using the starting materials listed in Table 1. The solutions contained 52.6 g of the pure element per liter of water for the elements labelled precursor in Table 1 and 5.26 g of the pure element per liter of water for the elements labelled promoter in Table 1.

TABLE 1

| starting material | role | element symbol |
|---|---|---|
| Cobalt(II)nitrate | precursor | Co |
| Chromium(III)nitrate | precursor | Cr |
| Iron(III)nitrate | precursor | Fe |
| Ammoniaheptamolybdate* 4 $H_2O$ | precursor | Mo |
| Lead(II)nitrate | precursor | Pb |
| Strontiumnitrate | precursor | Sr |
| Rhenium(VII)oxide | precursor | Re |
| Silvernitrate | precursor | Ag |
| Cesiumnitrate | promoter | Cs |
| Neodym(III)nitrate | promoter | Nd |
| Potassiumnitrate | promoter | K |
| Bismuthnitrate | precursor | Bi |
| Nickel(II)nitrate | precursor | Ni |
| Bariumnitrate | promoter | Ba |
| Europiumnitrate | promoter | Eu |
| Erbium(III)nitrate | promoter | Er |
| Sodiummetatungstenate | precursor | W |

According to the number of the elements required for a particular catalyst up to five aqueous solutions of the elements are dosed via micro syringe pumps into a 2 mL glass vessel. The total volume of the solutions in the glass vessel is 450 microliters. In Table 2 "composition" refers to the fraction of the corresponding aqueous element solution of the total volume of the solutions in the vessel. 1 g of $Al_2O_3$ is then added to the solution mixture. After the solution mixture is completely soaked up by the $Al_2O_3$ the material is dried overnight at ca. 100° C. and 200 mbar in a vacuum drying cabinet. The material is then calcined for 4 h at 500° C. in air. The catalyst is finally filled into a fixed bed reactor and conditioned for 4 h at 200° C. in a mixture of hydrogen and nitrogen (10% hydrogen of the total gas stream volume) with a flowrate of 0.08 l/h. At 200° C. and normal pressure, a gas stream composed of 24% propene, 4.5% oxygen and 71.5% air (percentages as fraction of total gas volume) is passed over the catalyst with a flowrate of 0.35 l/h. The effluent gas is tested with gas chromatography to determine the content of propylene oxide. In Table 2 "yield PO %" refers to the volume fraction of propylene oxide as part of the total volume in the effluent gas stream.

TABLE 2

| Example | Composition | Yield PO % |
|---|---|---|
| 10 | CoO, 3333 FeO, 3333 AgO, 3333 | 0.002804 |
| 11 | CoO, 3333 PbO, 3333 AgO, 3333 | 0.012592 |
| 12 | NiO, 3333 PbO, 3333 AgO, 3333 | 0.006409 |
| 13 | NiO, 3333 CoO, 3333 AgO, 3333 | 0.006942 |
| 14 | CoO, 25 FeO, 25 SrO, 25 AgO, 25 | 0.004742 |
| 15 | CoO, 25 PbO, 25 SrO, 25 AgO, 25 | 0.012488 |
| 16 | CoO, 25 PbO, 25 FeO, 25 AgO, 25 | 0.013624 |
| 17 | CoO, 25 CsO, 25 FeO, 25 AgO, 25 | 0.011009 |
| 18 | CoO, 25 CsO, 25 PbO, 25 AgO, 25 | 0.005510 |
| 19 | CoO, 25 BaO, 25 BiO, 25 AgO, 25 | 0.002667 |
| 20 | NiO, 25 PbO, 25 FeO, 25 AgO, 25 | 0.006396 |
| 21 | NiO, 25 CsO, 25 FeO, 25 AgO, 25 | 0.018402 |
| 22 | NiO, 25 CsO, 25 PbO, 25 AgO, 25 | 0.002536 |
| 23 | NiO, 25 BaO, 25 FeO, 25 AgO, 25 | 0.003577 |
| 24 | NiO, 25 BaO, 25 PbO, 25 AgO, 25 | 0.003900 |
| 25 | NiO, 25 CoO, 25 SrO, 25 AgO, 25 | 0.002614 |
| 26 | NiO, 25 CoO, 25 FeO, 25 AgO, 25 | 0.005089 |
| 27 | EuO, 25 ErO, 25 PbO, 25 WO, 25 | 0.008260 |
| 28 | MoO, 25 PbO, 25 SrO, 25 AgO, 25 | 0.001332 |
| 29 | FeO, 25 PbO, 25 SrO, 25 AgO, 25 | 0.001852 |
| 30 | FeO, 25 PbO, 25 SrO, 25 ReO, 25 | 0.002056 |
| 31 | FeO, 25 MoO, 25 SrO, 25 AgO, 25 | 0.004513 |
| 32 | CrO, 25 SrO, 25 ReO, 25 AgO, 25 | 0.002423 |
| 33 | CrO, 25 FeO, 25 ReO, 25 AgO, 25 | 0.001870 |
| 34 | CrO, 25 FeO, 25 SrO, 25 AgO, 25 | 0.002024 |
| 35 | CrO, 25 FeO, 25 PbO, 25 AgO, 25 | 0.002467 |
| 36 | CrO, 25 FeO, 25 MoO, 25 PbO, 25 | 0.003148 |
| 37 | CoO, 25 FeO, 25 MoO, 25 PbO, 25 | 0.001221 |
| 38 | CoO, 25 CrO, 25 ReO, 25 AgO, 25 | 0.002484 |
| 39 | CoO, 25 CrO, 25 PbO, 25 ReO, 25 | 0.001226 |
| 40 | CoO, 25 CrO, 25 PbO, 25 SrO, 25 | 0.001912 |
| 41 | CoO, 25 CrO, 25 MoO, 25 AgO, 25 | 0.001843 |
| 42 | CoO, 25 CrO, 25 FeO, 25 SrO, 25 | 0.002225 |
| 43 | CoO, 25 CrO, 25 FeO, 25 PbO, 25 | 0.001821 |
| 44 | CoO, 25 CrO, 25 FeO, 25 MoO, 25 | 0.002499 |
| 45 | CoO, 25 KO, 25 PbO, 25 AgO, 25 | 0.006633 |
| 46 | CoO, 25 NdO, 25 PbO, 25 AgO, 25 | 0.003476 |
| 47 | CoO, 25 FeO, 25 PbO, 25 AgO, 25 | 0.005896 |
| 48 | CoO, 25 FeO, 25 KO, 25 AgO, 25 | 0.008485 |
| 49 | CoO, 25 CsO, 25 PbO, 25 AgO, 25 | 0.006147 |
| 50 | CoO, 25 CsO, 25 FeO, 25 AgO, 25 | 0.008464 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the epoxidation of hydrocarbons comprising:
   (1) reacting
      (a) at least one hydrocarbon
   with
      (b) oxygen or air or nitrous oxide or other gaseous oxidants,
   in the presence of
      (c) a mixture comprising at least two elements selected from the group consisting of Sc, Y, Ti, Zr, Hf, V, Nb, Ta, Cr, Mo, W, Re, Fe, Co, Ni, Sn, Pb, Sb, Bi and Se, on a support with a BET surface area of less than 200 $m^2/g$.

2. The process of claim 1, wherein the BET surface area of said support is less than 100 $m^2/g$.

3. The process of claim 1, wherein the support comprises $Al_2O_3$.

4. The process of claim 1, wherein (a) said hydrocarbon is selected from the group consisting of propylene and butylene.

5. The process of claim 1, wherein (c) said mixture comprising at least two elements is selected from the group consisting of: CoFe, CoRe, CoCr, CoNi, NiCr, Co—Fe, Co—Re, Co—Cr, Co—Ni, Ni—Cr, Sb—Fe, Co—Fe—Ag, Co—Pb—Ag, Ni—Pb—Ag, Ni—Co—Ag, Co—Fe—Sr—Ag, Co—Pb—Sr—Ag, Co—Pb—Fe—Ag, Co—Cs—Fe—Ag, Co—Cs—Pb—Ag, Co—Ba—Bi—Ag, Ni—Pb—Fe—Ag, Ni—Cs—Fe—Ag, Ni—Cs—Pb—Ag, Ni—Ba—Fe—Ag, Ni—Ba—Pb—Ag, Ni—Co—Sr—Ag, Ni—Co—Fe—Ag, Eu—Er—Pb—W, Mo—Pb—Sr—Ag, Fe—Pb—Sr—Ag, Fe—Pb—Sr—Re, Fe—Mo—Sr—Ag, Cr—Sr—Re—Ag, Cr—Fe—Re—Ag, Cr—Fe—Sr—Ag, Cr—Fe—Pb—Ag, Cr—Fe—Mo—Pb, Co—Fe—Sr—Ag, Co—Cr—Re—Ag, Co—Cr—Pb—Re, Co—Cr—Pb—Sr, Co—Cr—Mo—Ag, Co—Cr—Fe—Sr, Co—Cr—Fe—Pb, Co—Cr—Fe—Mo, Co—K—Pb—Ag, Co—Nd—Pb—Ag, Co—Fe—Pb—Ag, Co—Fe—K—Ag, Co—Cs—Pb—Ag, Co—Cs—Fe—Ag and SbFe.

6. A catalyst for the epoxidation of hydrocarbons, wherein said catalyst comprises a mixture comprising at least two elements selected from the group consisting of Sc, Y, Ti, Zr, Hf, V, Nb, Ta, Cr, Mo, W, Re, Fe, Co, Ni, Sn, Pb, Sb, Bi and Se, on a support with a BET surface area of less than 200 $m^2/g$.

7. The catalyst of claim 6, wherein the mixture comprising at least two elements is selected from the group consisting of CoFe, CoRe, CoCr, CoNi, NiCr and SbFe.

* * * * *